United States Patent [19]

Müller et al.

[11] Patent Number: 4,582,405

[45] Date of Patent: Apr. 15, 1986

[54] OPHTHALMOLOGICAL COMBINATION INSTRUMENT FOR DIAGNOSIS AND TREATMENT

[75] Inventors: Ortwin Müller, Aalen; Kurt Schulz; Albrecht Vogel, both of Oberkochen; Gerhard Hanemann, Oberkochen; Gerhard Müller, Aalen; Gunther Kürbitz; Arnold Güttner, both of Königsbronn, all of Fed. Rep. of Germany

[73] Assignee: Carl-Zeiss-Stiftung, Heidenheim on the Brenz, Fed. Rep. of Germany

[21] Appl. No.: 644,796

[22] Filed: Aug. 27, 1984

[30] Foreign Application Priority Data

Sep. 1, 1983 [DE] Fed. Rep. of Germany ....... 3331586

[51] Int. Cl.⁴ .............................................. A61B 3/10
[52] U.S. Cl. .................................... 351/221; 351/205; 351/214
[58] Field of Search ......................... 351/205, 214, 221

[56] References Cited

U.S. PATENT DOCUMENTS 3,096,767  7/1963  Gresser et al. ................. 351/221 X Primary Examiner—Rodney B. Bovernick
Attorney, Agent, or Firm—Stonebraker, Shepard & Stephens

[57] ABSTRACT

An Nd:YAG laser of small size with a passive quality switch is combined with a slit-lamp instrument, to form an ophthalmological combination instrument for diagnosis and treatment. By a plurality of pulses within a pulse train, which succeed each other within the $\mu$ sec range, particularly good therapeutic effects are obtained. A second laser, emitting continuous visible radiation, has its beam aligned with the beam of invisible radiation from the first laser, and shows the user at all times the location of the beam of invisible radiation. The visible beam of radiation is split into two beams separated from each other by a light-free zone, and there is provision for blocking and unblocking these two beams alternately, which produces an effect which greatly aids the user in accurate focusing. This combination instrument affords the user the possibility of making a diagnosis and following it immediately by treatment.

18 Claims, 7 Drawing Figures

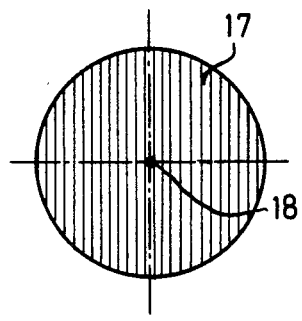
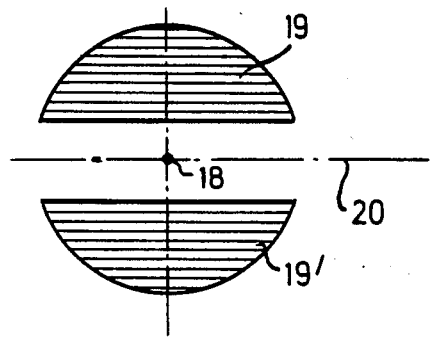
Fig. 4a  Fig. 4b
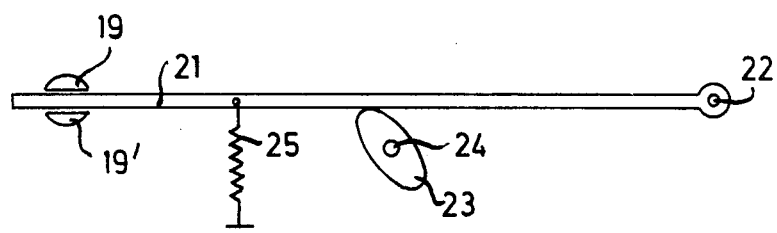
Fig. 5

OPHTHALMOLOGICAL COMBINATION INSTRUMENT FOR DIAGNOSIS AND TREATMENT

BACKGROUND OF THE INVENTION

The present invention relates to a combination instrument useful both for examining the eye and for treating the eye. It comprises a stereoscopic viewing microscope and an associated unit.

One form of ophthalmological combination instrument is disclosed in German Federal Republic Pat. No. 26 14 273 (Carl Zeiss), of Feb. 15, 1979, and its similar British Pat. No. 1,575,244, of Sept. 17, 1980. That instrument comprises a diagnostic instrument in which a slit lamp, constructed in accordance with the principle of a binocular telescope magnifier, can be converted into an ophthalmometer by the insertion of another optical part after removal of the main objective of the stereoscopic viewing microscope.

It is also known to provide an operation microscope which can be combined with a laser system for purposes of treatment. Such instruments are disclosed, for example, in U.S. Pat. No. 3,096,767 (Gresser et al.) of July 9, 1963, and U.S. Pat. No. 3,769,963 (Goldman et al.) of Nov. 6, 1973. In these two patents, the therapeutic laser radiation is guided outside the viewing instrument or operation microscope.

If one attempts to combine a laser system for therapy purposes with a stereoscopic viewing microscope, according to the combining principles disclosed in the above mentioned German Pat. No. 26 14 273, there would have to be available a laser of small size, the radiation of which can be conducted through the viewing lens system of the binocular viewing microscope. Surprisingly, it has been found that a laser which is particularly well suited for this purpose is a neodymium-yag pulse laser (Nd:yag laser), known from range finder systems, which has a passive quality switch (Q switch). This known laser has the characteristic that upon an increase in the intensity of the pumping light it emits, in one pulse sequence, not just one individual pulse, but rather a pulse chain of several (e.g., up to five) individual pulses, the time spacing beteen the pulses being 10 to $2\mu$ sec and the energy of the individual pulses being about 15 to 10 mJ.

For the previous field of use of this known laser (i.e., in rangefinder systems), this property is undesired, and is avoided by suitable selection of the operating conditions. However, this property has been found to be useful for the treatment of cataracts of the eye. Such laser pulses produce, upon focusing, spontaneous ionization of the material and thereby destroy the protein fibrils which cause clouding of the lens or vitreous body of the eye.

It has been found that, for proper guidance of the therapeutic effect, specifically this spontaneous collapse of material and the mechanical shock wave connected therewith which leads to the cracking of the protein fibrils are the important factors. The above mentioned Nd:yag laser is excellently suited for the intended therapeutic purpose when it is operated with a sufficiently high pumping-light energy. Likewise, this laser can also be used to advantage for perforating the lens membrane or the iris itself.

SUMMARY OF THE INVENTION

The object of the invention is to provide a handy combination instrument useful both for diagnosis and for treatment, based on the principles of combination known from the mentioned German Pat. No. 26 14 273.

According to the invention, this object is attained by providing, as an auxiliary unit, a combination of two lasers or laser systems. The first laser system emits pulsewise in the invisible region, producing a plurality of individual pulses each having a duration of about 5 n sec, time spaced from each other by about $10\mu$ sec, energy of about 15-20 mJ being produced in one pumping. The second laser of this combination emits continuously in the visible region, its beam having a cross section which consists of two individual beams with a light-free zone between them. The centroid beams of the visible laser radiation and the invisible laser radiation lie along the same axis. The two individual beams of the visible laser radiation are alternately connectable and disconnectable.

Conversion filters and laser protection filters are advisedly provided in the viewing ray path.

In one advantageous embodiment of the invention, the individual beams of the visible laser radiation have the cross section of a circular sector and are alternately connected and disconnected by means of an electric circuit.

The connecting and disconnecting of the individual beams can also be done by a bar diaphragm moved back and forth over the cross section of the beam. In another advantageous embodiment, the bar diaphragm consists of spring wire which is moved back and forth by a motor driven rotating eccentric or cam.

One particularly favorable construction is the provision of a T-shaped housing for holding the mechanical-optical parts of the laser treatment attachment, this housing being located above the horizontal plane of the microscope axes of the viewing system and having the operating controls of the attachment on the front of this housing, that is, the side toward the user of the apparatus (the surgeon).

The advantages resulting from the invention include, in particular, the fact that the laser system combines an extremely small volume with ease of modification of the energy of the pumping light. Furthermore, the invention facilitates the work of the surgeon by a focusing aid for the laser therapy beam and an extremely favorable ergonomic arrangement of the operating elements. The user can use the slit lamp, an item with which he is already acquanted, in the ordinary manner for diagnostic purposes, and after completing the diagnosis, he can commence the treatment by means of the easily operated therapeutic attachment unit, the T-shape of the housing permitting the user to have a good view of the patient.

Treatment with successive pulses furthermore has the advantage that the second pulse is even more effectively absorbed in the plasma which was produced by the first pulse by spontaneous ionization of the material, as a result of which the therapeutic effect is improved. Thus a method results which can be carried out easily and reliably in order to set locally large lesions. For smaller lesions, the energy can be weakened by means of gray filters.

One embodiment of the invention is illustrated in the drawings, and will be described in further detail below.

BRIEF DESCRIPTION OF THE DRAWINGS

FIG. 3 is a schematic sectional view along a plane at right angles to the plane of FIG. 2a;

FIG. 4a is an illustration of the crosssectional shape of the beam from one of the lasers of the combination instrument;

FIG. 4b is a similar view of the beam from the other one of the lasers; and

FIG. 5 is an illustration of a switch mechanism for the sector beam of the laser emitting in the visible region.

DESCRIPTION OF THE PREFERRED EMBODIMENT

Figure 1:
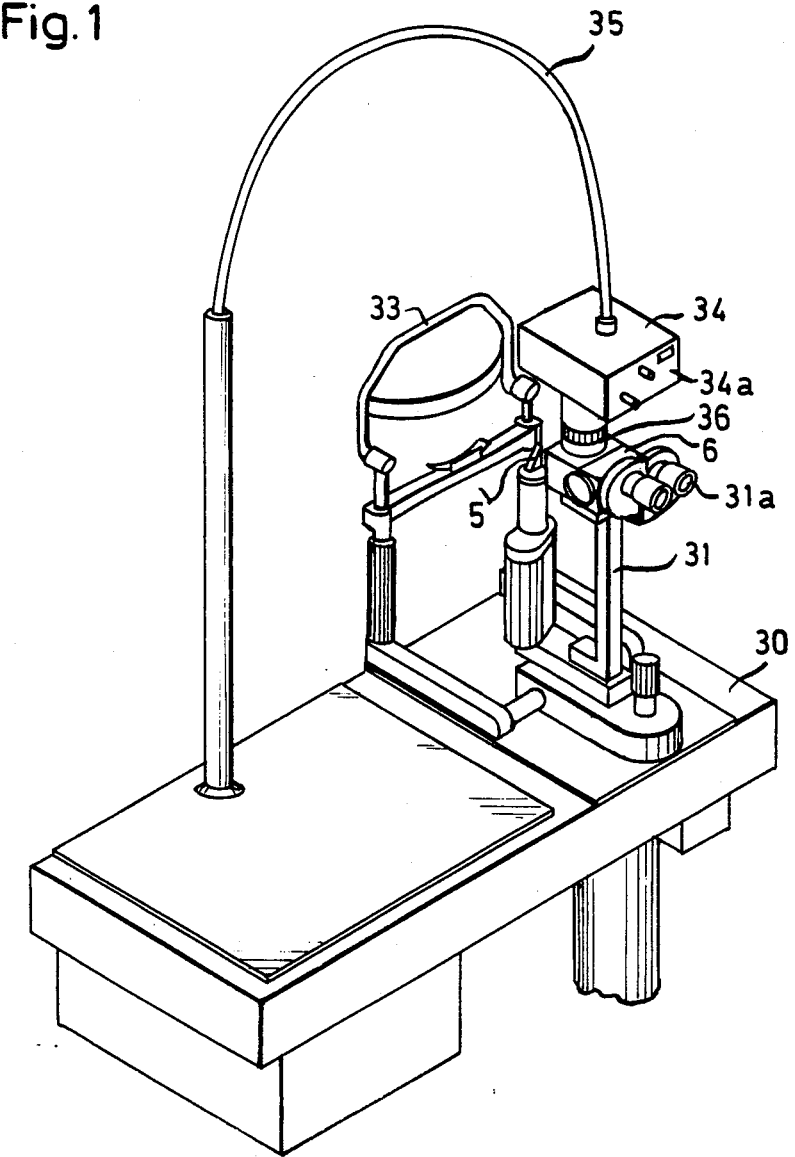
FIG. 1 is a perspective view of a combination instrument according to a preferred embodiment of the invention.

Referring first to FIG. 1, there is shown a work table 30 on which the combination instrument of the invention is mounted. The stereoscopic viewing microscope of a conventional slit lamp apparatus is supported by the post 31, and the slit illumination device is shown at 5 (see also FIG. 2a). When the head of the patient is placed against the head rest 33, the eyes of the patient may be seen by the user of the instrument through the binocular eyepiece 31a.

The laser housing 34, containing the two lasers, is of T-shape, having a wide upper portion held above the normal eye level of the user by a narrower lower portion 36 which, in turn, is supported from the optical housing 6 at the top of the post 31. This T-shaped configuration provides the necessary space for the laser parts in the wide upper portion, above the user's eye level, but the lower portion, at the user's eye level, is much narrower and does not interfere seriously with the user's ability to look at the patient. The operating controls for the lasers are on the front plate 34a of the housing 34, i.e., on the side toward the user, in an accessible position for easy operation. Energy is supplied to the lasers through a supply cable 35 from the table 30.

Figures 2A, 2B:
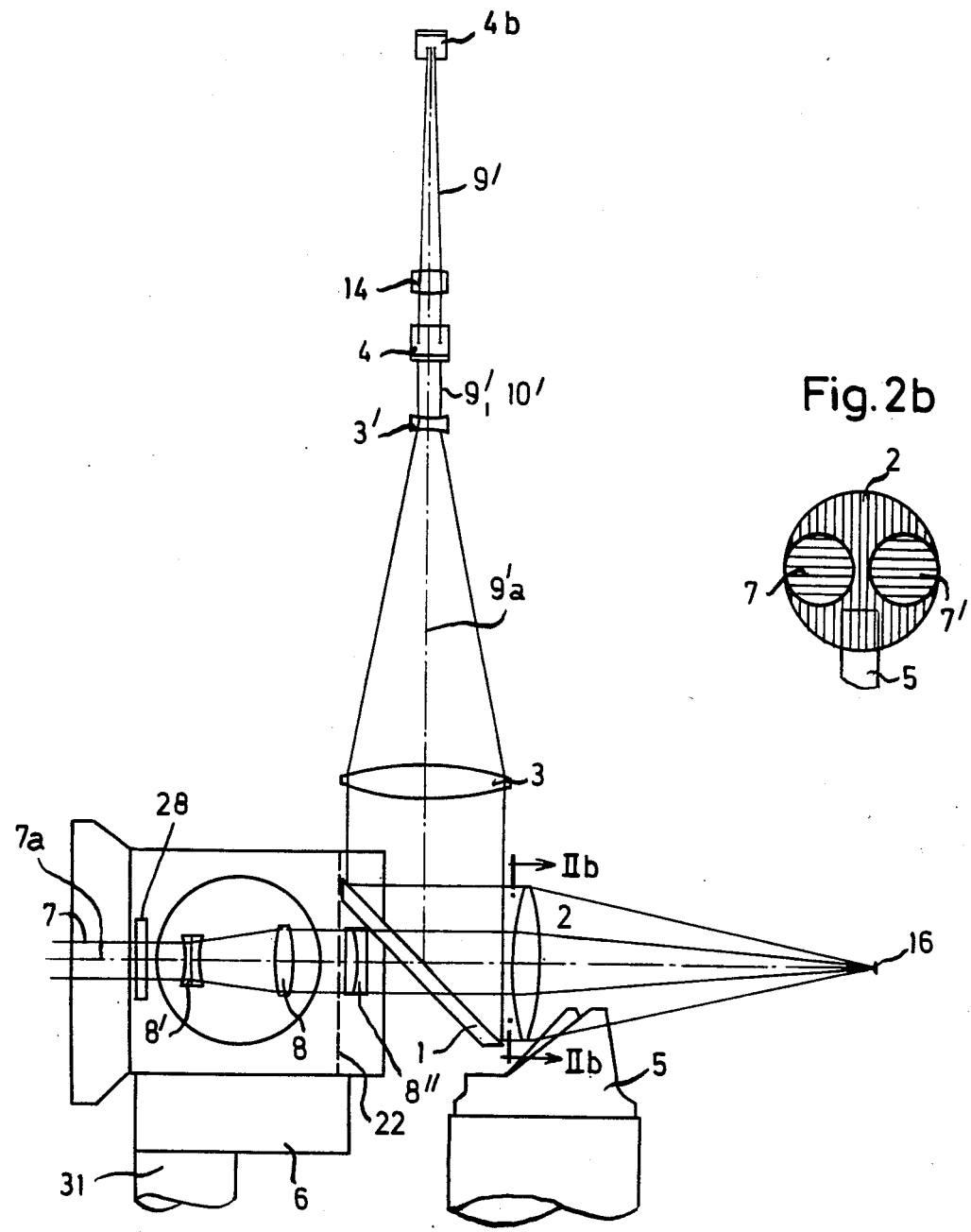
FIG. 2a is a schematic sectional view along the main axis of the combination instrument, showing the mechanicaloptical principles.
FIG. 2b is a schematic crosssection across the ray paths through the main focusing objective.
Figure 3:
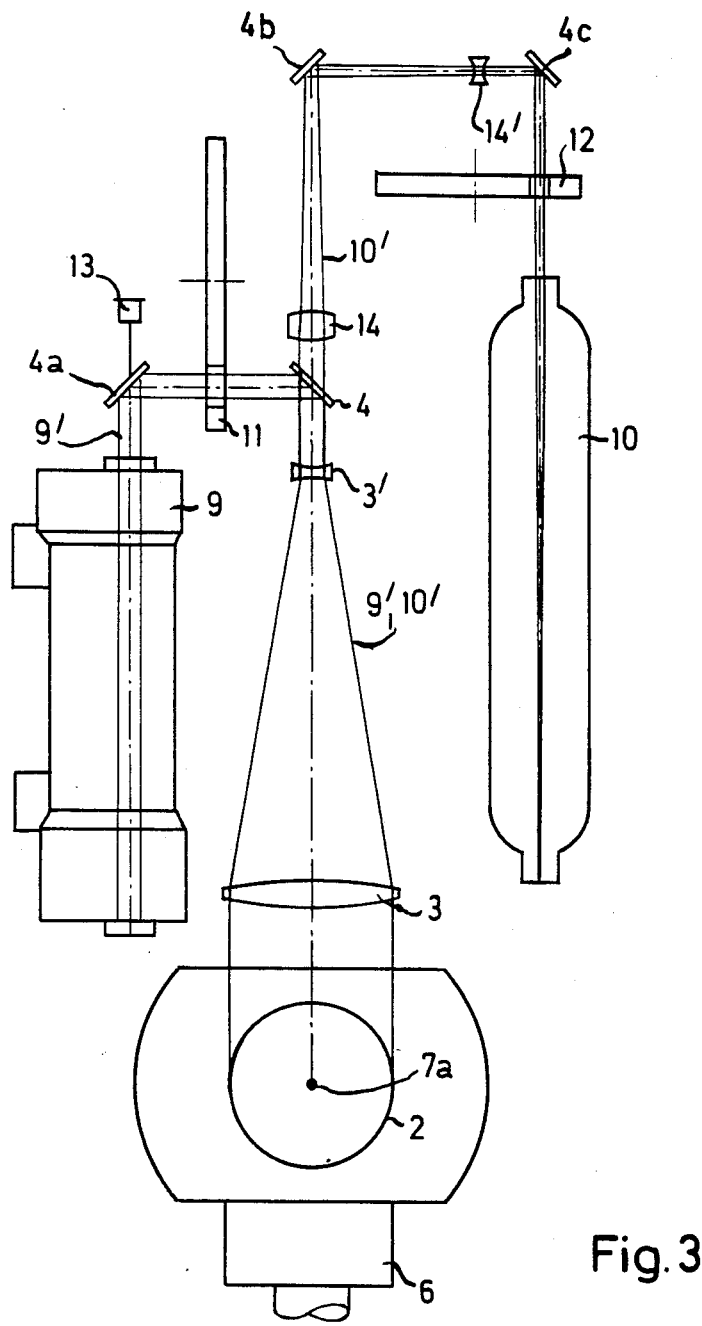

Referring now to FIGS. 2a and 3, some of the parts shown here are shown also in FIG. 1 and have already beeen described. The observation ray path is indicated at 7. In this path there are arranged the known Galileo magnification changer elements 8 and 8', with an auxiliary system 8". The place of separtion, or interface, of the combination instrument is indicated by the broken line 22 in FIG. 2a. To the right of this line 22 the main objective of the stereoscopic microscope is normally located. But to provide the combination instrument of the present invention, this main objective is removed, and is replaced by the attachment of the present invention, i.e. the T-shaped housing 34, 36 containing the two lasers and other parts as herein described.

The slit illumination is shown at 5 in FIG. 2a as well as FIG. 1. It is illustrated in central position in FIG. 2b.

The coupling part of the laser therapy instrument comprises the beam splitter plate 1 and the main focusing objective 2. The centroid beam of the viewing ray path is marked 7a. The centroid beam of the laser rays coincide with this viewing path 7a from the splitter plate 1 onward to the focus point 16 at the eye of the patient.

For producing ther laser therapy radiation, an Nd:YAG laser is used, for the reasons already explained above. A HeNe laser is used as the marking laser beam instrument. Both lasers are arranged in the housing 34. Eye protection filters and conversion filters 28 are arranged in the ray path to the eyes of the user.

In FIG. 3, the Nd:YAG laser is shown at 9, and the He-Ne laser at 10. Since the beam of the He-Ne laser has a smaller cross-section than that of the Nd:YAG laser, the beam 10' emitted by the He-Ne laser is widened by a telescopic system 14', 14 before it is combined coaxially at the beam splitter plate 4 with the therapy laser beam 9' from the laser 9. By a further telescope system 3', 3 the two laser ray paths, now coaxial with each other, are widened to the diameter of the objective 2, thereby obtaining a large radiation aperture. A receiver 13 measures the energy of the Nd:yag laser pulses. The reflecting mirrors 4a, 4b, and 4c serve to guide the laser beams along their respective paths as illustrated, the mirror 4a allowing some of the energy to pass through so as to be measured by the receiver or meter 13 above mentioned.

In the embodiment of the invention illustrated diagrammatically in FIGS. 2a and 3, the invisible pulsed neodymium-YAG radiation 9' is marked or indicated by the He-Ne laser continuous light beam 10'. The two radiation beams are coaxial and are focused at the point 16, at the eye of the patient being treated. Because of the fixed association of the two lasers, the user can be certain that he knows the focus of the dangerous yag laser radiation at all times and under all conditions. For better focusing, however, the cross sections of the two laser beams are different, as will be explained in further detail with reference to FIGS. 4a and 4b.

As shown in FIG. 4a, the Nd:YAG radiation 17 fills a circular cross-section around the axis 18. Contrasted with this, the cross-section of the beam from the He-Ne marker laser is in two parts 19 and 19', as shown in FIG. 4b, each part being a sector of a circle, separated from each other and symmetrical with respect to the axis 18 and to a horizontal axis 20.

The radius of the circle from which these two sectors 19 and 19' are formed is greater than the radius of the circle 17 of the Nd:yag laser radiation. In this way it is assured that the Nd:yag radiation is always emitted within the cone of the He-Ne light. A merging of the two individual beams 19 and 19' takes place only at the focusing point 16. In every other transverse plane, the two beams 19 and 19' are separated by a zone which is free of light. This is a great help to the user in focusing. It also has the result that the focus which is produced on the axis 18 can be seen with good contrast in the optical medium, since no scattered or reflected light can be produced in the masked region between the two individual beams 19 and 19'.

A focusing aid mechanism is illustrated in FIG. 5. Here, the two individual sector beams 19 and 19' are alternately disconnected and connected (blocked and unblocked) by shutter means. If the ray paths are alternately cut or blocked at a plane which is not identical with the focusing plane, then the user has the impression that the light projections which he sees are blinking, and this is found to assist accurate focusing.

The illustrated mechanism for accomplishing this focusing enhancement comprises primarily a bar diaphragm 21 which is moved back and forth across the cross-section of the beam, perpendicular to the direction of the beam. This is done by means of a motor driven eccentric or cam 23 which turns on its axis 24 and acts on the diaphragm bar 21 to raise it on its pivotal axis 22 against the action of a spring 25 which pulls the bar downwardly. As the cam rotates, the diaphragm will rise and fall, blocking alternately the two visible radiation sectors 19 and 19'.

Because of the only slight divergence of the laser radiation, the shutter mechanism can be installed in front of the beam expansion system, and thus can be made very small. A further simplification of the shutter mechanism is possible, wherein the bar diaphragm is itself of elastic material, such as a spring wire, clamped fast at one end and acted upon by the eccentric or cam as above described. If the diaphragm itself is a spring wire or made of other elastic material, this eliminates the need for the pivot 22 and the return spring 25.

The frequency of the blinking of this focusing device is preferably about one Hz (one cycle per second). It can be varied to suit the preference of the user, by changing the speed of the driving motor (usually a small electric motor) which rotates the eccentric or cam 24. Also, this dynamic focusing aid may be placed completely out of action very easily, if preferred by the user, simply by pulling the diaphragm member up to a position where it does not obstruct the beam, and securing it in that position.

Since the modulation transfer function for the individual QCams is 100% while in the focusing plane it is at most 50%, the user has the impression that the focal point is constant in time. The dynamic focusing means above described is of great advantage especially when the focus is to be imaged into a system of reflective spherical surfaces, such as the eye represents. The reflections can lead to points of virtual focus which must not be confused with the true point of focus, which alone is subject to refraction at such surfaces. The danger of confusion is present also for the reason that the intensity of the reflections as seen by the viewer may be greater than the intensity of the true focus point, which is indicated to the user, after all, only by scattering and scatter reflection in the medium. The dynamic focusing means above described has the effect that all points of reflection blink, and they represent themselves differently to the left viewing path than to the right viewing path. Only the true point of focus is seen with both the right eye and the left eye of the user with approximately the same intensity and relative quiet.

What is claimed is:

1. An ophthalmological combination instrument comprising a stereoscopic viewing microscope and an auxiliary unit, said auxiliary unit including first laser means and second laser means, said first laser means having means for emitting pulsewise invisible radiation providing a plurality of individual pulses each having a duration of about 5 n sec, the individual pulses being time spaced from each other by about 10μ sec, an energy of about 15 mJ being produced in one pumping operation, said radiation emitted by said first laser means forming a first beam, said second laser means having means for emitting continuous visible radiation to form a second beam which, in cross section, consists of two individual beams with a light-free zone between them, and means for directing said first beam and said second beam along a common axis toward an object to be observed or treated.

2. The invention defined in claim 1, wherein said combination instrument includes an observation ray path along which a user of said instrument may observe said object, further comprising conversion filter means and laser protection filter means interposed in said observation ray path.

3. The invention defined in claim 1, wherein said two individual beams of said second beam each have a cross section in the shape of a sector of a circle.

4. The invention defined in claim 1, further comprising means for alternately blocking and unblocking said two individual beams of said second beam.

5. The invention defined in claim 4, wherein said means for blocking and unblocking comprises a bar diaphragm moved back and forth over the cross section of said second beam.

6. The invention defined in claim 5, wherein said bar diaphragm is so shaped and positioned that when it completely blocks one of said individual beams of said second beam, the other of said individual beams is completely unblocked, and vice versa.

7. The invention defined in claim 5, wherein said means for alternately blocking and unblocking includes resilient means tending to move said bar diaphragm to an unblocking position, and rotary operating means for shifting said bar diaphragm to a blocking position.

8. The invention defined in claim 7, wherein said bar diaphragm is a pivoted member, and said resilient means is a separate spring operatively connected to said pivoted member.

9. The invention defined in claim 7, wherein said rotary operating means is a motor driven eccentric member.

10. The invention defined in claim 7, wherein said bar diaphragm is an elastic member one part of which is held in fixed position, and said resilient means is inherent resilience of said elastic member.

11. The invention defined in claim 10, wherein said elastic member is a spring wire.

12. The invention defined in claim 1, further comprising electric switch means for rendering said two beams of said second radiation beam alternately effective and ineffective.

13. The invention defined in claim 1, wherein said combination instrument has a microscope viewing system with viewing axes, further comprising a housing arranged at least mainly above said viewing axes, said housing containing substantially all mechanical-optical parts of said first laser means and said second laser means.

14. The invention defined in claim 13, wherein said housing has operating controls for said first and second laser means arranged on a side of said housing faced toward a user of said combination instrument.

15. The invention defined in claim 13, wherein said housing is of generally T-shape, having a wide upper portion at an elevation substantially above said viewing axes where such wide portion will not interfere with a user's view of a patient on the other side of the instrument from the user, and a substantially narrower lower portion serving to support said wide upper portion.

16. The invention defined in claim 1, wherein said first laser means includes an Nd:YAG laser.

17. The invention defined in claim 1, wherein said second laser means includes a He-Ne laser.

18. The invention defined in claim 1, wherein said first laser means includes an Nd:YAG laser and said second laser means includes a He-Ne laser.

* * * * *